(12) United States Patent
Morris et al.

(10) Patent No.: US 7,152,598 B2
(45) Date of Patent: *Dec. 26, 2006

(54) SYSTEM AND METHOD FOR PROVIDING A BREATHING GAS

(75) Inventors: Make Morris, Shreveport, LA (US); Gregory William Flolid, North Royalton, OH (US); Neal Joseph Curran, Lakewood, OH (US)

(73) Assignee: Invacare Corporation, Elyria, OH (US)

( * ) Notice: Subject to any disclaimer, the term of this patent is extended or adjusted under 35 U.S.C. 154(b) by 85 days.

This patent is subject to a terminal disclaimer.

(21) Appl. No.: 10/601,720

(22) Filed: Jun. 23, 2003

(65) Prior Publication Data

US 2004/0255943 A1    Dec. 23, 2004

(51) Int. Cl.
*A61M 16/00* (2006.01)

(52) U.S. Cl. ............. 128/204.23; 128/204.18; 128/204.21

(58) Field of Classification Search ......... 128/204.18, 128/204.21, 204.23, 205.23, 205.24, 205.18, 128/200.24, 204.22

See application file for complete search history.

(56) References Cited

U.S. PATENT DOCUMENTS

| | | | |
|---|---|---|---|
| 4,011,859 A | 3/1977 | Frankenberger |
| 4,350,166 A | 9/1982 | Mobarry |
| 4,506,678 A | 3/1985 | Russell et al. |
| 4,648,396 A | 3/1987 | Raemer |
| 4,655,213 A | 4/1987 | Rapoport et al. |
| 4,713,558 A | 12/1987 | Russell et al. |
| 4,728,499 A | 3/1988 | Fehder |
| 4,773,411 A | 9/1988 | Downs |
| 4,817,013 A | 3/1989 | Corenman et al. |
| 4,821,736 A | 4/1989 | Watson |
| 4,944,310 A | 7/1990 | Sullivan |
| 4,994,117 A | 2/1991 | Fehder |
| 5,065,756 A | 11/1991 | Rapoport |
| 5,117,819 A | 6/1992 | Servidio et al. |
| 5,124,129 A | 6/1992 | Riccitelli et al. |
| 5,134,995 A | 8/1992 | Gruenke et al. |
| 5,148,802 A | 9/1992 | Sanders et al. |
| 5,166,075 A | 11/1992 | Fehder |
| 5,179,002 A | 1/1993 | Fehder |
| 5,193,544 A | 3/1993 | Jaffe |
| 5,199,424 A | 4/1993 | Sullivan et al. |
| 5,203,343 A | 4/1993 | Axe et al. |
| 5,239,995 A | 8/1993 | Estes et al. |
| 5,245,995 A | 9/1993 | Sullivan et al. |
| 5,279,289 A | 1/1994 | Kirk |
| 5,313,937 A | 5/1994 | Zdrojkowski |
| 5,332,901 A | 7/1994 | Eckles et al. |
| 5,335,654 A | 8/1994 | Rapoport |
| 5,343,878 A | 9/1994 | Scarberry et al. |
| 5,353,788 A | 10/1994 | Miles |
| 5,394,882 A | 3/1995 | Mawhinney |
| 5,433,193 A | 7/1995 | Sanders et al. |
| 5,438,980 A | 8/1995 | Phillips |
| 5,445,160 A | 8/1995 | Culver et al. |
| 5,456,249 A | 10/1995 | Kirk |

(Continued)

*Primary Examiner*—Teena Mitchell
(74) *Attorney, Agent, or Firm*—Calfee, Halter & Griswold LLP

(57) ABSTRACT

Systems and methods of providing a breathing gas are provided. The method includes, for example, sensing a parameter associated with the delivery of a breathing gas, changing a valve position in response to a change in the sensed parameter, determining a breathing state based on the valve position, and causing a change in the sensed parameter of the breathing gas based on the determined breathing state.

31 Claims, 5 Drawing Sheets

U.S. PATENT DOCUMENTS

| | | |
|---|---|---|
| 5,458,137 A | 10/1995 | Axe et al. |
| 5,490,502 A | 2/1996 | Rapoport et al. |
| 5,492,113 A | 2/1996 | Estes et al. |
| 5,503,146 A | 4/1996 | Froehlich et al. |
| 5,522,382 A | 6/1996 | Sullivan et al. |
| RE35,295 E | 7/1996 | Estes et al. |
| 5,535,738 A | 7/1996 | Estes et al. |
| 5,535,739 A | 7/1996 | Rapoport et al. |
| 5,537,997 A | 7/1996 | Mechlenburg et al. |
| 5,540,219 A | 7/1996 | Mechlenburg et al. |
| 5,546,933 A | 8/1996 | Rapoport et al. |
| 5,549,106 A | 8/1996 | Gruenke et al. |
| 5,551,418 A | 9/1996 | Estes et al. |
| 5,551,419 A | 9/1996 | Froehlich et al. |
| 5,558,638 A | 9/1996 | Evers et al. |
| RE35,339 E | 10/1996 | Rapoport |
| 5,592,938 A | 1/1997 | Scarberry et al. |
| 5,598,838 A | 2/1997 | Servidio et al. |
| 5,630,411 A | 5/1997 | Holscher |
| 5,632,269 A | 5/1997 | Zdrojkowski |
| 5,655,522 A | 8/1997 | Mechlenburg et al. |
| 5,679,884 A | 10/1997 | Kirk |
| 5,682,878 A | 11/1997 | Ogden |
| 5,694,923 A | 12/1997 | Hete et al. |
| 5,701,883 A | 12/1997 | Hete et al. |
| 5,704,345 A | 1/1998 | Berthon-Jones |
| 5,715,812 A | 2/1998 | Deighan et al. |
| 5,738,106 A | 4/1998 | Yamamori et al. |
| 5,740,795 A | 4/1998 | Brydon |
| 5,765,563 A | 6/1998 | Vander Schaaf |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport et al. |
| 5,823,187 A | 10/1998 | Estes et al. |
| 5,845,636 A | 12/1998 | Gruenke et al. |
| 5,865,173 A | 2/1999 | Froehlich |
| 5,881,717 A | 3/1999 | Isaza |
| 5,881,723 A | 3/1999 | Wallace et al. |
| 5,901,704 A | 5/1999 | Estes et al. |
| 5,904,141 A | 5/1999 | Estes et al. |
| 5,915,379 A | 6/1999 | Wallace et al. |
| 5,915,380 A | 6/1999 | Wallace et al. |
| 5,927,274 A | 7/1999 | Servidio et al. |
| 5,937,851 A | 8/1999 | Serowski et al. |
| 5,947,115 A | 9/1999 | Lordo et al. |
| 5,953,713 A | 9/1999 | Behbehani et al. |
| 5,954,050 A | 9/1999 | Christopher |
| 5,970,975 A | 10/1999 | Estes et al. |
| 6,017,315 A | 1/2000 | Starr et al. |
| 6,024,089 A | 2/2000 | Wallace et al. |
| 6,026,312 A | 2/2000 | Shemwell et al. |
| 6,029,660 A | 2/2000 | Calluaud et al. |
| 6,029,664 A | 2/2000 | Zdrojkowski et al. |
| 6,029,665 A | 2/2000 | Berthon-Jones |
| 6,044,843 A | 4/2000 | O'Neil et al. |
| 6,085,747 A | 7/2000 | Axe et al. |
| 6,091,973 A | 7/2000 | Colla et al. |
| 6,095,974 A | 8/2000 | Shemwell et al. |
| 6,099,481 A | 8/2000 | Daniels et al. |
| 6,102,042 A | 8/2000 | Hete et al. |
| 6,105,575 A | 8/2000 | Estes et al. |
| 6,123,074 A | 9/2000 | Hete et al. |
| 6,123,075 A | 9/2000 | Kirk |
| 6,135,106 A | 10/2000 | Dirks et al. |
| 6,138,675 A | 10/2000 | Berthon-Jones |
| 6,142,952 A | 11/2000 | Behbehani et al. |
| 6,152,129 A | 11/2000 | Berthon-Jones |
| 6,155,986 A | 12/2000 | Brydon et al. |
| 6,182,657 B1 | 2/2001 | Brydon et al. |
| 6,183,423 B1 | 2/2001 | Gaumond et al. |
| 6,212,435 B1 | 4/2001 | Lattner et al. |
| 6,213,119 B1 | 4/2001 | Brydon et al. |
| 6,237,592 B1 | 5/2001 | Surjadi et al. |
| 6,237,593 B1 | 5/2001 | Brydon |
| 6,240,921 B1 | 6/2001 | Brydon et al. |
| 6,253,764 B1 | 7/2001 | Calluaud |
| 6,257,234 B1 | 7/2001 | Sun |
| 6,269,811 B1 | 8/2001 | Duff et al. |
| 6,269,812 B1 | 8/2001 | Wallace et al. |
| 6,279,569 B1 | 8/2001 | Berthon-Jones |
| 6,299,581 B1 | 10/2001 | Rapoport et al. |
| 6,302,105 B1 | 10/2001 | Wickham et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,349,724 B1 * | 2/2002 | Burton et al. .......... 128/204.18 |
| 6,357,463 B1 * | 3/2002 | Wickham et al. ............. 137/12 |
| 6,443,154 B1 * | 9/2002 | Jalde et al. ............ 128/205.29 |
| 6,467,477 B1 | 10/2002 | Frank et al. |
| 6,609,517 B1 | 8/2003 | Estes et al. |
| 6,745,770 B1 * | 6/2004 | McAuliffe et al. ..... 128/205.24 |
| 6,752,151 B1 * | 6/2004 | Hill ...................... 128/204.18 |
| 6,766,800 B1 * | 7/2004 | Chu et al. .............. 128/205.24 |
| 6,823,866 B1 * | 11/2004 | Jafari et al. ............ 128/204.21 |
| 6,866,040 B1 * | 3/2005 | Bourdon ................. 128/204.18 |
| 6,895,964 B1 * | 5/2005 | McAuliffe et al. ..... 128/205.24 |
| 2001/0004894 A1 | 6/2001 | Bourdon |
| 2001/0015204 A1 | 8/2001 | Hansen et al. |
| 2001/0027791 A1 | 10/2001 | Wallace et al. |
| 2001/0027792 A1 | 10/2001 | Berthon-Jones et al. |
| 2001/0035186 A1 | 11/2001 | Hill |
| 2001/0035187 A1 * | 11/2001 | Smith et al. ........... 128/205.24 |
| 2002/0104536 A1 * | 8/2002 | Richey, II ............... 128/204.22 |
| 2003/0159695 A1 * | 8/2003 | Younes .................. 128/204.18 |
| 2004/0035422 A1 * | 2/2004 | Truitt et al. ............ 128/204.18 |
| 2004/0103896 A1 * | 6/2004 | Jafari et al. ............ 128/204.18 |
| 2005/0034724 A1 * | 2/2005 | O'Dea .................. 128/204.18 |

* cited by examiner

SYSTEM AND METHOD FOR PROVIDING A BREATHING GAS

FIELD OF THE INVENTION

The invention relates generally to the delivery of a breathing gas to an airway of a patient, and more particularly, to the delivery of a breathing gas coordinated with the breathing cycle of the patient.

BACKGROUND

Obstructive sleep apnea is an airway breathing disorder caused by relaxation of the muscles of the upper airway to the point where the upper airway collapses or becomes obstructed by these same muscles. It is known that obstructive sleep apnea can be treated through the application of pressurized air to the nasal passages of a patient. The application of pressurized air forms a pneumatic splint in the upper airway of the patient thereby preventing the collapse or obstruction thereof.

Within the treatment of obstructive sleep apnea, there are several known CPAP regimens including, for example, mono-level CPAP and bi-level CPAP. Mono-level CPAP involves the constant application of a single therapeutic or medically prescribed CPAP level. That is, through the entire breathing cycle, a single therapeutic positive air pressure is delivered to the patient. While such a regimen is successful in treating obstructive sleep apnea, some patients experience discomfort when exhaling because of the level of positive air pressure being delivered to their airways during exhalation.

In response to this discomfort, bi-level CPAP regimens were developed. Bi-level CPAP involves delivering a higher therapeutic CPAP during inhalation and a lower therapeutic CPAP during exhalation. The higher therapeutic CPAP level is commonly known as inspiratory positive airway pressure or "IPAP." The lower therapeutic CPAP level is commonly known as expiratory positive airway pressure or "EPAP." Since the EPAP is lower than the IPAP, the patient needs to do less work during exhalation to exhale and thus experiences less discomfort, compared to the mono-level CPAP regimen.

However, the development of bi-level CPAP significantly increased the sophistication of CPAP devices because the devices must accurately determine when the patient is inhaling and exhaling and to properly coordinate the IPAP and EPAP levels thereto. One approach is to determine the instantaneous and average flow rates of air being delivered to the patient and then to compare the two to determine whether a patient was inhaling or exhaling. If the instantaneous flow rate is greater than the average flow rate, the patient is deemed to be inhaling. If the instantaneous flow rate is less than the average flow rate, the patient is deemed to be exhaling.

While CPAP has been useful in the treatment of obstructive sleep apnea and other respiratory related illnesses such as, for example, chronic obstructive pulmonary disease and neuro-muscular disorders affecting the muscles and tissues of breathing, it is highly desirable to provide additional ways of delivering a therapeutic breathing gas to a patient.

SUMMARY

According to one embodiment, a method of providing a breathing gas is described. The method includes, for example, sensing a parameter associated with the delivery of a breathing gas, changing a valve position in response to a change in the sensed parameter, determining a breathing state based on the valve position, and causing a change in the sensed parameter of the breathing gas based on the determined breathing state.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

DETAILED DESCRIPTION OF ILLUSTRATED EMBODIMENTS

Prior to discussing the various embodiments, a review of the definitions of some exemplary terms used throughout the disclosure is appropriate. Both singular and plural forms of all terms fall within each meaning:

"Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desire manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

"breathing state," as used herein, includes any state or combination of states where air is drawn into the lungs and/or expelled from the lungs. For example, a first breathing state may be associated with drawing air into the lungs and a second breathing state may be associated with expelling air from the lungs. Additionally, a breathing state can have one or more sub-states. For example, the start of inhalation can be a breathing state and the end of inhalation can be another breathing state, with the range therebetween defining one or more other breathing states. Similarly, the start and end of exhalation, and the range there between, can also be defined by one or more breathing states.

Figure 1:
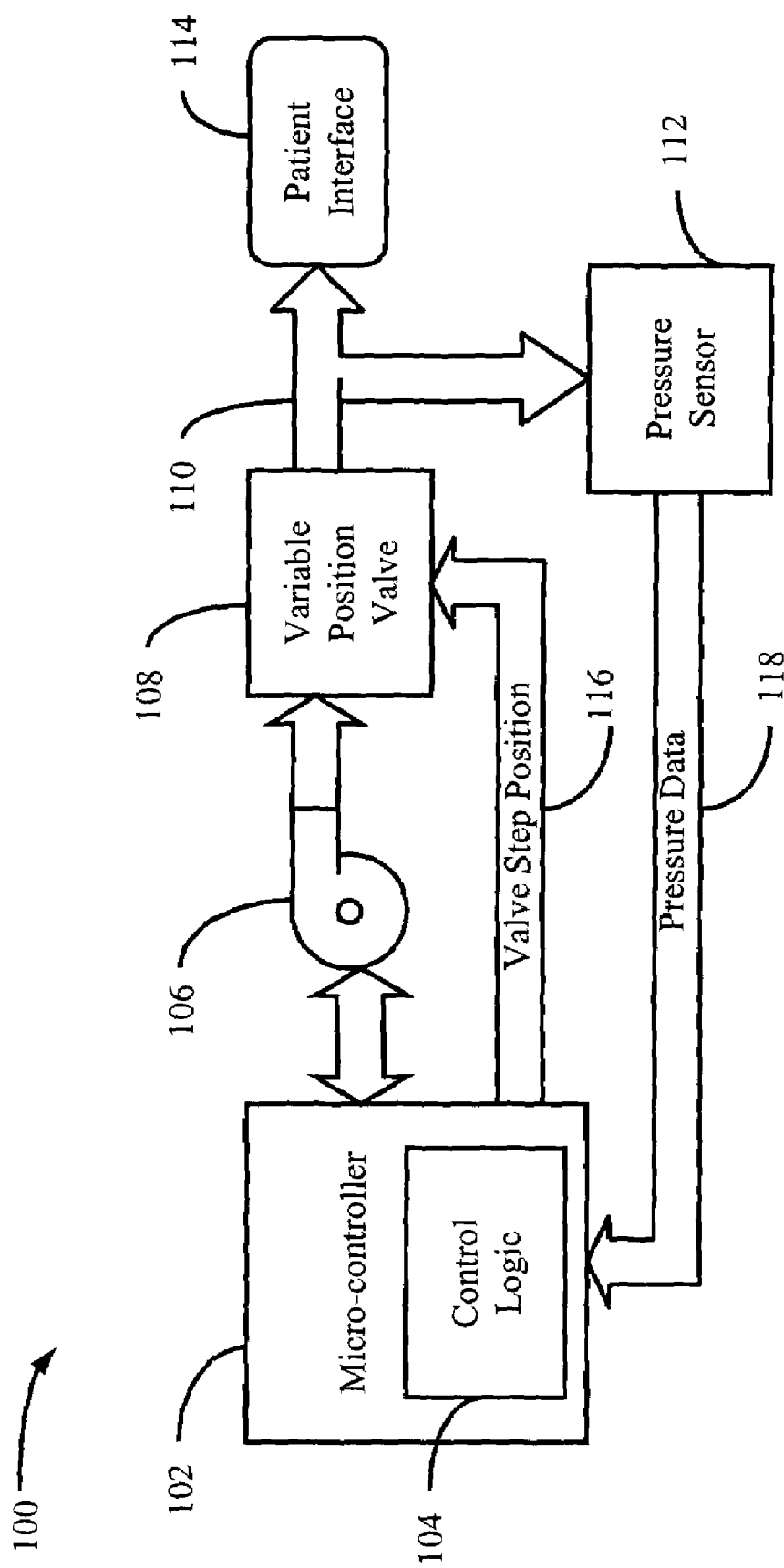
FIG. 1 is one embodiment of functional block diagram illustrating a system for delivering a breathing gas.

The systems and methods described herein are particularly suited for assisting the respiration of spontaneously breathing patients, though they may also be applied to other respiratory regimens including, for example, acute and homecare ventilation. Referring now to FIG. 1, block diagram 100 illustrating one embodiment of a system is shown. The system has a controller 102 with control logic 104, a blower 106, a variable position poppet valve 108 with a bi-directional stepper motor and a pressure sensor 112. A flow path 110 provides a path for a flow of breathable gas from the valve 108 to a patient interface 114. Patent interface 114 can be any nasal mask, face mask, cannula, or similar device. Pressure sensor 112 senses a parameter of the breathing gas such as the pressure in flow path 110, which is associated with and indicative of the pressure in the patient interface 114. The controller 102 is preferably processor-based and can various input/output circuitry including analog-to-digital (A/D) inputs and digital-to-analog (D/A) outputs. The controller 102 sends valve step position data 116 to the valve 108 to control its position and the sensor 112 sends pressure data 118 back to the controller 102 to be read.

The valve step position is preferably defined by the stepper motor specification and can include step positions that are less than 1 step or a whole step. Generally, the valve step position can range from any negative number to any positive number. One preferable valve step position range includes 0 to 100, where step position 0 is associated with a fully closed valve position and step 100 is associated with a fully open valve position. Therefore, for a given blower speed and valve configuration, each valve step position can be determined to be equivalent to an approximate pressure change (e.g., a valve step position equals a pressure change of 0.2 cm $H_2O$.)

While the embodiment of FIG. 1 has been described with reference to a flow/pressure control element in the form of a variable position valve 108 and a sensor element in the form of a pressure sensor 112, the flow/pressure control and sensor elements can include other types of devices. For example, the flow/pressure control element can be a variable speed blower with a linear valve or solenoid valve, alone or in combination with a stepper motor controlled variable position valve. The sensor element can include a flow sensor, temperature sensor, infra-red light emitter/sensor, motor current sensor, or motor speed sensor alone or in combination with the pressure sensor. The data generated from these sensor(s) is fed back to the controller 102 for processing.

In one aspect, a system for delivering a breathing gas to a patient interface is provided. In one embodiment, the system includes a pressure sensor, a blower, a valve, and a controller connected to the sensor, blower and valve. The controller includes a memory having a plurality of executable instructions. The plurality of executable instructions include: i) a first set of instructions sensing a pressure associated with the delivery of the breathing gas to the patient interface, a second set of instructions changing the valve position in response to a change in the sensed pressure, a third set of instructions detecting a start of inhalation state by determining if the valve position has increased beyond a start of inhalation state threshold value, a fourth set of instructions detecting an end of inhalation state by determining if the valve position has fallen below an end of inhalation state threshold value, a fifth set of instructions delivering the breathing gas at least at a first positive pressure above ambient pressure after detection of the start of inhalation state, and a sixth set of instructions delivering the breathing gas at least at a second pressure after detection of the end of inhalation state wherein the second pressure is less than the first pressure.

In another embodiment, the plurality of executable instructions also includes a seventh set instructions delivering the breathing gas from the second pressure to the first pressure according to a predefined function and prior to the detection of the next start of inhalation state. In a variation of this embodiment, the predefined function is a linear function. In another variation of this embodiment, the predefined function is associated with a sensed pressure associated with the patient interface. In still another variation of this embodiment, the second pressure comprises at least an ambient pressure.

Figure 2:
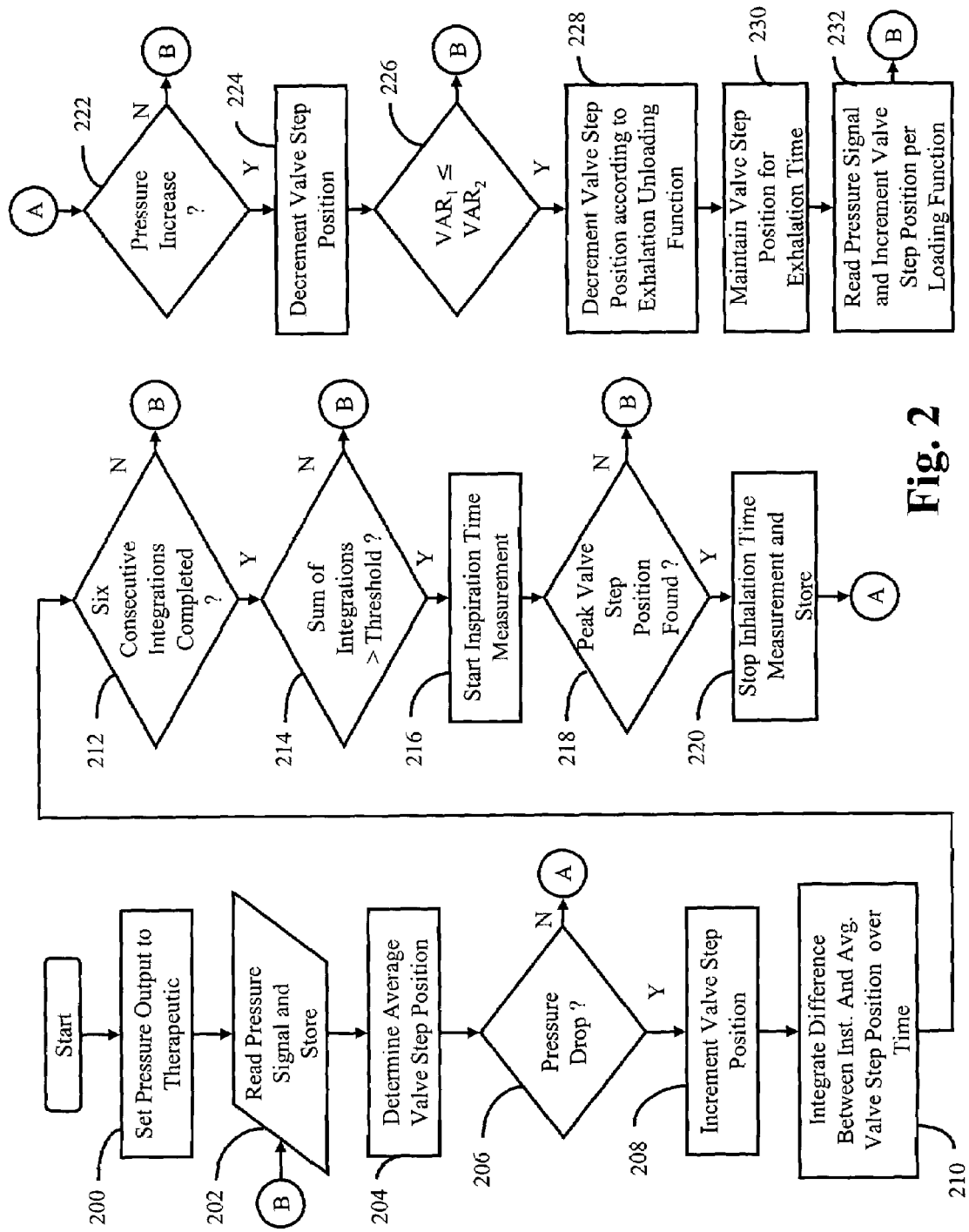
FIG. 2 is one embodiment of a flowchart illustrating the control of the system.

Referring now to FIG. 2, the operation of the system will be described with reference to the flowchart illustrated therein. In the flowchart, the rectangular elements denote processing blocks and represent software instructions or groups of instructions. The quadrilateral elements denote data input/output processing blocks and represent software instructions or groups of instructions directed to the input or reading of data or the output or sending of data. The flow diagrams shown and described herein do not depict syntax of any particular programming language. Rather, the flow diagrams illustrate the functional information one skilled in the art may use to fabricate circuits or to generate software to perform the processing of the system. It should be noted that many routine program elements, such as initialization of loops and variables and the use of temporary variables are not shown.

In block 200, the controller 102 opens the valve 108 and sets the blower 106 to a speed that produces a predetermined pressure at the its output. This predetermined pressure is generally set to a medically prescribed positive pressure for a patient, plus an additional pressure of 5 cm $H_2O$, via a pressure-to-speed look-up table that is stored in the memory of the controller 102. While an additional pressure of 5 cm $H_2O$ has been described, other pressures including no additional pressure can be chosen as well. The medically prescribed positive pressure is typically a pressure that is above the ambient pressure and can range anywhere from 2 to 20 cm $H_2O$. Once the blower 106 is set to provide the set pressure, it is rarely, if ever, changed during active operation of the device. Instead, the controller 102 uses the step position of the valve 108 to modulate the output pressure through both a closed loop and an open loop control. The closed loop control is a function of sensed pressure and the open loop control is a function of time. Together, these control loops direct the operation of the system through the breathing cycle of a patient. It should also be noted that the closed loop and open loop control can also be based on other parameters such as, for example, instantaneous and average flow rates, temperature of the gases in the patient interface, and/or composition of the gases (e.g. $CO_2$) in the patient interface.

In block 202, pressure is read and stored for subsequent processing. In block 204, an average valve step position is determined and maintained or updated. In step 206, the controller 102 determines if a pressure drop has been sensed. This is preferably accomplished by comparing the presently sensed pressure with the immediately preceding sensed pressure. If the presently sensed pressure is less, then a pressure drop has occurred and the flow proceeds to block 208. In block 208, the controller 102 increments the valve step position to compensate for the pressure drop. Incrementing the valve step position has the effect of increasing the flow and pressure of the breathing gas delivered from the valve's output. The step position is change iteratively until the error or difference between the sensed pressures is minimized. During this phase of operation, the controller 102 seeks to maintain a constant pressure in the flow path 112 until patient exhalation is sensed.

In block 210, the difference between the instantaneous and average valve position is integrated over time and stored in memory. The summation of six such integrations is used to determine the start of an inhalation breathing state by determining if the summation is greater than a start of inhalation threshold (blocks 212 and 214). If the summation is greater than the threshold, the start of the inhalation breathing state has occurred and a timer begins the measurement of the inhalation breathing state in block 216. This measurement continues until a peak valve step position has been found in block 218. The peak valve step position is determined by comparing the previous valve step position to the present valve step position and saving in memory the step position that is greater as the peak valve step position. If the peak valve step position remains unchanged for some time period (e.g., 80 ms), then the controller 102 assumes that the peak valve step position has occurred for this inhalation phase and stops the inhalation breathing state time measurement in block 220. The peak valve step position is a threshold indicative of the imminent end of the inhalation breathing state.

In block 222, the controller 102 tests to determine if a pressure increase has occurred by reading the pressure signal. If a pressure increase has occurred after a peak valve step position has been found, then the inhalation breathing state is imminently ending. Block 224 decrements the valve position to lower the flow and pressure provided so as to maintain a constant pressure in the air flow path. This is once again accomplished by an iterative process by which the error between the presently sensed pressure and the previously sensed pressure is minimized. Block 226 tests to determine if the inhalation breathing state has ended by comparing two variables, $VAR_1$ and $VAR_2$. These variables are defined as follows:

$$VAR_1 = (\text{Inst. Step Position}) - (\text{Avg. Step Position})$$

$$VAR_2 = [(\text{Peak Step Position}) - (\text{Avg. Step Position})] * \text{Threshold}$$

The variable "Threshold" is a percentage value such as, for example, 0.85, though other percentage values can also be chosen. If $VAR_1 \leq VAR_2$, then the inhalation breathing state has ended and the exhalation breathing state has or is about to commence.

Block 228 decrements the valve step position according an exhalation unloading function that lowers the pressure delivered over time so that the pressure initially delivered during the exhalation breathing state is less than the pressure delivered during the inhalation breathing state. The pressure is dropped until a predetermined minimum pressure is provided, which can include ambient pressure. This lower pressure is maintained in block 230 for an exhalation time period that is generally equal to 2.5 times the measured inhalation state time period. Multiples other than 2.5 can also be selected after the expiration of this time period, the pressure signal is read in block 232 and the valve step position is incremented according to a pressure loading function. The pressure loading function reads the present pressure and returns over time the output pressure to the medically prescribed positive pressure, where the system once again looks for a start of inhalation breathing state.

In this manner, a positive pressure is provided during the inhalation phase of a breathing cycle to assist the patient in inhalation and a lower pressure is provided during the exhalation phase of a breathing cycle to allow the patient to exhalation against a lower pressure. Such a system provides a level of comfort over other types of Continuous Positive Airway Pressure delivery in that the patient is not required to exhale against the same pressure used during inhalation for any appreciable period of time.

Figure 3:
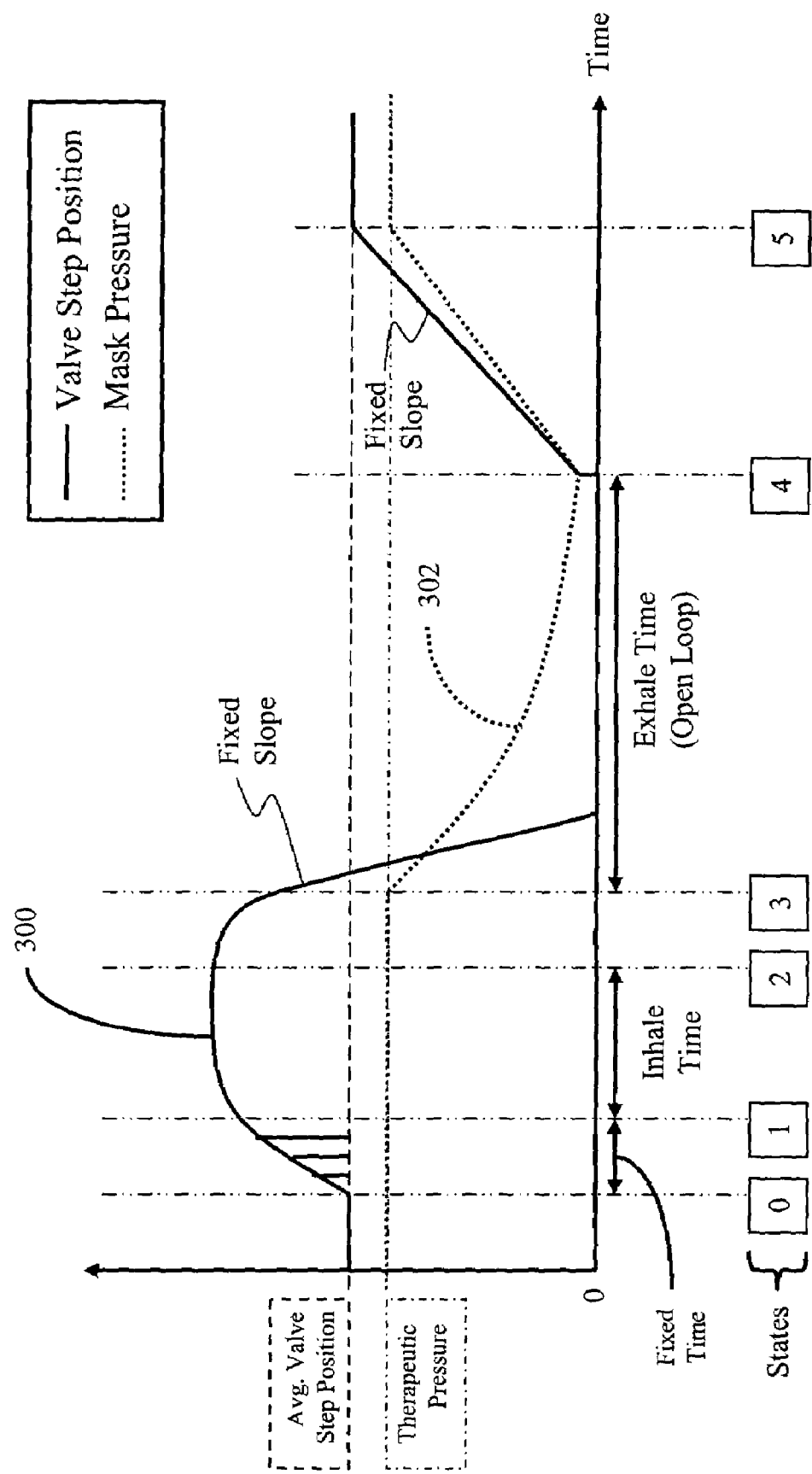
FIG. 3 is a graph illustrating the valve step position and mask pressure over time for one embodiment of the invention.

Referring now to FIG. 3, a chart illustrating a valve step position curve 300 and an output pressure curve 302 as a function of time is shown. The two curves have been overlaid to more clearly illustrate the synchronization between pressure and valve step position. The operation description will now be reviewed with reference to the curves of FIG. 3.

Prior to state 0, the system is in the closed loop control and is sensing the pressure at its output via its pressure sensor. Since there is very little pressure change prior to state 0, the system is maintaining a constant valve step position, which results in a constant output pressure (preferably, the medically prescribed positive pressure). This typically occurs at the end of patient exhalation where there is very little pressure change in the system caused by the patient.

When the patient begins to inhale, a pressure drop is sensed by the pressure sensor 112. This pressure drop causes the system to further open the valve 108 in a step-wise fashion to compensate for the drop in pressure caused by patient inhalation. During such inhalation, the system attempts to maintain an output pressure substantially equivalent to the medically prescribed positive pressure. Each step position of the valve is equivalent to a known approximate pressure change (e.g., 0.2 cm $H_2O$). The difference between the sensed pressure and the set pressure (i.e., the medically prescribed positive pressure) generates an error value, which the system attempts to minimize by appropriately adjusting the valve step position, which appropriately adjusts the pressure delivered.

State 0 occurs when the valve step position is increased and triggers a fixed time period which leads to State 1. During this fixed time period, the difference between the instantaneous valve step position and the average valve step position is integrated over 6 time intervals. FIG. 3 shows only 3 intervals for the sake of clarity. If the summation of these 6 integrations is greater than a threshold value, then a patient inhalation is assumed and an inhalation timer is started that measures the time of inhalation.

This inhalation time measurement is terminated when a peak valve step position has been reached in State 2. The peak valve step position is determined by comparing the previous valve step position to the present valve step position and saving in memory the step position that is greater as the peak valve step position. If the peak valve step position remains unchanged for some time period (e.g., 80 ms), then the system assumes that the peak valve step position has occurred for this inhalation phase.

After State 2, the system looks for an exhalation trigger. This is accomplished by comparing two variables, both of which are based on valve step position. The equations have defined above as $VAR_1$ and $VAR_2$. If $VAR_1 \leq VAR_2$ then the trigger exists and the system moves to State 3.

In State 3, the system closes the variable position valve 108 so as to provide a lower pressure at its output. The valve 108 can be quickly and linearly closed (e.g., with a fixed slope of 3 ms/step) by reducing the valve step position to, for example, position 0 (i.e., closed). During a significant portion of exhalation, the system now provides a lower pressure than that used during inhalation. This makes it easier for the patient to exhale.

From State 3 to State 4, the system is in open-loop control and does not vary the valve step position based on pressure or any other parameter. The valve remains in its step position during this fixed time period. As described above, the time period can be fixed to be 2.5 times the previously determined inhalation time (i.e., time from State 1 to State 2). This is the pressure unloading portion of the system operation.

At State 4, the exhalation time period expires and the system gradually applies pressure to its output until the pressure once again reaches the medically prescribed positive pressure. The system is now re-loading the pressure at its output. This is accomplished by sensing the pressure at State 4, which is caused primarily by patient exhalation, and quickly changing the valve step position to meet that pressure. Hence, this phase of exhalation starts with a pressure that is dependent on the patient exhalation pressure. From State 4 to State 5, the system gradually changes the valve step position in a linear fashion (e.g., with a fixed slope of 40 ms/step) thereby gradually opening the valve until the output pressure once again reaches the higher medically prescribed positive pressure. The system is now ready for the next patient inhalation where the process repeats.

Figure 4:
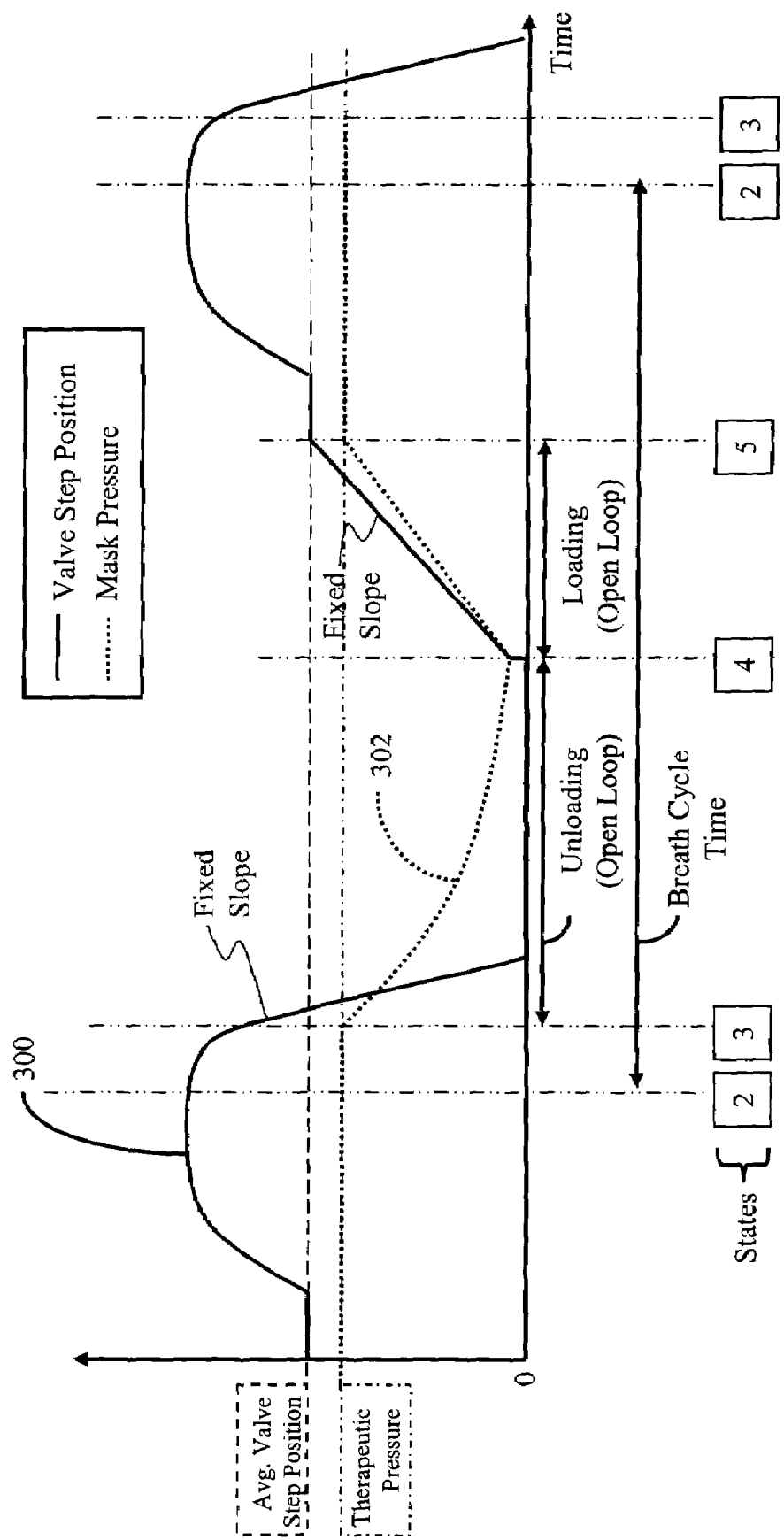
FIG. 4 is a graph illustrating the valve step position and mask pressure over time for another embodiment of the invention.

FIG. 4 illustrates an embodiment of the invention directed to exhalation trigger-based control. In this regard, the control is the similar to that explained above, except that no inhalation trigger is provided. In particular, a breath cycle time is measured as a function of the peak valve step position. The time between two peak valve step positions (State 2) is a measure of the breathing cycle time. The exhalation trigger at State 3, unloading portion from States 3 to 4, and loading portion from States 4 to 5 are the same as described above in connection with FIG. 3. The unloading portion (States 3 to 4) and loading portion (States 4 to 5) are defined to be percentages of the breath cycle time of the previous breath cycle (s). These percentages can range broadly, but are typically chosen that the unloading and loading portion together are any where from about 50% to 85% of the breath cycle time. The advantage of this embodiment is that it requires less processing by the controller 102.

Figure 5:
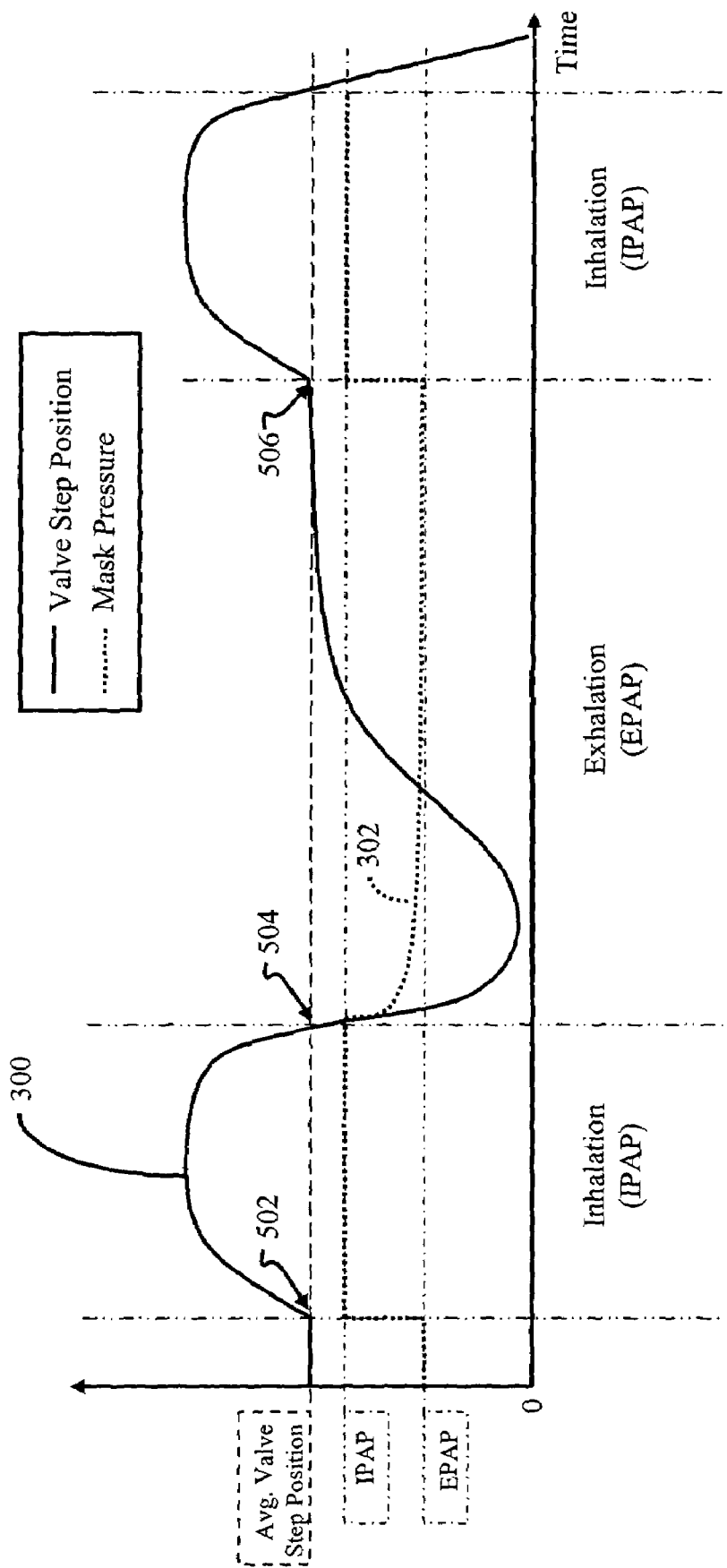
FIG. 5 is a graph illustrating the valve step position and mask pressure over time for yet another embodiment of the invention.

Illustrated in FIG. 5 is an embodiment of the present invention that uses the instantaneous and average valve step position to detect the breathing state of a patient than coordinates the pressure delivered according to the detected states. In this embodiment, the system is in closed-loop control mode where it is always sensing the pressure and adjusting its output based thereon. More specifically, as the patient breathes, an average valve step position is established by virtue of the valve step position increasing to raise the pressure delivered for inhalation and decreasing to reduce the pressure delivered for exhalation based on the pressure fed back to the controller 102. By comparing the instantaneous valve step position to the average valve step position, the breathing state of the patient can be detected. If the instantaneous valve step position is above the average valve step position, the patient is inhaling. If the instantaneous valve step position is below the average valve step position, the patient is exhaling. To reduce premature or erratic triggering, the average valve step position can be offset above its true value for inhalation detection and below its true value for exhalation detection.

In FIG. 5, reference 502 indicates the instantaneous valve step position crossing the average valve step position with a positive slope. This indicates the patient is inhaling because the valve is increasing its step position to compensate for the drop in pressure caused by the patient inhalation. Reference 504 indicates the instantaneous valve step position crossing the average valve step position with a negative slope. This indicates the patient is exhaling because the valve is decreasing its step position to compensate for the increase in pressure caused by patient exhalation. According to such detection, an IPAP level can be applied during inhalation and an EPAP level can be applied during exhalation. Reference 506 indicates the next inhalation detection.

While the present invention has been illustrated by the description of embodiments thereof, and while the embodiments have been described in considerable detail, it is not the intention of this specification to restrict or in any way limit the scope of the appended claims to such detail. Additional advantages and modifications will readily appear to those skilled in the art. For example, valve step position can be changed according to non-linear function as an alternate, addition or in combination with linear functions. Alternate or additional parameters of the flow gas can be sensed including flow rates through the use of flow sensors to modulate valve step position. More specifically, the direction of flow and/or the change in flow rates (e.g., instantaneous and average) can also be used. Therefore, the invention, in its broader aspects, is not limited to the specific details, the representative apparatus, and illustrative examples shown and described. Accordingly, departures may be made from such details without departing from the spirit or scope of the applicant's general inventive concept.

What is claimed is:

1. A system for delivering a breathing gas to a patient interface comprising:
    a pressure sensor;
    a blower;
    a valve;
    a controller connected to the sensor, blower and valve, the controller comprising a memory having a plurality of executable instructions, wherein the executable instructions comprise:
        a first set of instructions sensing a pressure associated with the delivery of the breathing gas to the patient interface;
        a second set of instructions changing the valve position in response to a change in the sensed pressure;
        a third set of instructions detecting a start of inhalation state by determining if the valve position has increased beyond a start of inhalation state threshold value;
        a fourth set of instructions detecting an end of inhalation state by determining if the valve position has fallen below an end of inhalation state threshold value;
        a fifth set of instructions delivering the breathing gas at least at a first positive pressure above ambient pressure after detection of the start of inhalation state; and
        a sixth set of instructions delivering the breathing gas at least at a second pressure after detection of the end of inhalation state wherein the second pressure is less than the first pressure.

2. The system of claim 1 further comprising a seventh set instructions delivering the breathing gas from the second pressure to the first pressure according to a predefined function and prior to the detection of the next start of inhalation state.

3. The system of claim 2 wherein the predefined function is a linear function.

4. The system of claim 2 wherein the predefined function is associated with a sensed pressure associated with the patient interface.

5. The system of claim 2 wherein the second pressure comprises at least an ambient pressure.

6. A system for providing a breathing gas, including:
means for sensing a parameter associated with delivery of the breathing gas;
first means for changing a control parameter associated with a control element in response to a difference between the sensed parameter and a first predetermined value during an inhalation state of a breathing cycle;
means for determining a transition from the inhalation state to an exhalation state of the breathing cycle based at least in part on the control parameter;
second means for changing the control parameter to cause a first change in the sensed parameter during an unload portion of the exhalation state based at least in part on the determined transition; and
third means for changing the control parameter to cause a second change in the sensed parameter during a load portion of the exhalation state based at least in part on the first predetermined value.

7. The system of claim 6 wherein the sensed parameter is gas pressure, gas flow, gas temperature, or gas composition.

8. The system of claim 6 wherein the control element includes a variable position valve and the control parameter includes a valve step position.

9. The system of claim 6 wherein the control element includes a variable speed blower and the control parameter includes a blower speed.

10. The system of claim 6 wherein the determining means includes means for determining an average valve step position.

11. The system of claim 6 wherein the determining means includes means for identifying an instantaneous valve step position.

12. The system of claim 6 wherein the determining means includes means for determining a peak valve step position.

13. The system of claim 6 wherein the transition from the inhalation state to the exhalation state is based at least in part on a predetermined percentage threshold value.

14. The system of claim 6 wherein the second changing means includes means for determining an inhale time associated with the inhalation state.

15. The system of claim 6 wherein changing the control parameter to cause the first change in the sensed parameter during the unload portion is based at least in part on an unloading function.

16. The system of claim 6 wherein changing the control parameter to cause the first change in the sensed parameter during the unload portion is based at least in part on a second predetermined value.

17. The system of claim 6 wherein the second means for changing includes means for determining a peak valve step position.

18. The system of claim 6 wherein changing the control parameter to cause the second change in the sensed parameter during the load portion is based at least in part on a loading function.

19. An apparatus for providing a breathing gas, including:
means for sensing a breathing gas pressure associated with delivery of the breathing gas;
means for detecting a start of an inhalation state of a breathing cycle;
first means for changing a valve step position associated with a variable position valve in response to a difference between the sensed breathing gas pressure and a first predetermined breathing gas pressure value during the inhalation state;
means for determining a transition from the inhalation state to an exhalation state of the breathing cycle based at least in part on the changing valve step position;
second means for changing the valve step position to cause a first change in the breathing gas pressure during an unload portion of the exhalation state based at least in part on the determined transition; and
third means for changing the valve step position to cause a second change in the breathing gas pressure during a load portion of the exhalation state based at least in part on the first predetermined breathing gas pressure value.

20. The apparatus of claim 19, the detecting means including:
means for determining an average valve step position;
means for integrating a difference between an instantaneous valve step position and the average valve step position over a predetermined integration time to produce a summation; and
means for identifying the start of the inhalation state after the summation is greater than a predetermined start of inhalation threshold value.

21. The apparatus of claim 19, the determining means including:
means for calculating a first transition variable based at least in part on an instantaneous valve step position;
means for calculating a second transition variable based at least in part on a peak valve step position; and
means for identifying the transition from the inhalation state to the exhalation state after the first transition variable is less than or equal to the second transition variable.

22. The apparatus of claim 19, the second changing means including:
means for determining an inhale time associated with the inhalation state;
means for determining an exhale time associated with the unload portion of the exhalation state and based at least in part on the determined inhale time;
means for beginning the exhale time after the transition from the inhalation state to the exhalation state;
means for decrementing the valve step position according to an unloading function until a second predetermined breathing gas pressure value is achieved; and
means for changing the valve step position in response to a difference between the sensed breathing gas pressure and the second predetermined breathing gas pressure value after the second predetermined breathing gas pressure value is achieved and until the exhale time expires.

23. The apparatus of claim 19, the third changing means including:
means for incrementing the valve step position according to a loading function until the first predetermined breathing gas pressure value is achieved; and
means for changing the valve step position in response to a difference between the sensed breathing gas pressure and the first predetermined breathing gas pressure value after the first predetermined breathing gas pressure value is achieved.

24. An apparatus for providing a breathing gas, including:
means for sensing a breathing gas pressure associated with delivery of the breathing gas;

first means for determining a breath cycle time associated with at least a portion of a current inhalation state of a current breathing cycle and a portion of a previous breathing cycle;

first means for changing a valve step position associated with a variable position valve in response to a difference between the sensed breathing gas pressure and a first predetermined breathing gas pressure value during the current inhalation state;

second means for determining a transition from the current inhalation state to a current exhalation state of the current breathing cycle based at least in part on the changing valve step position;

second means for changing the valve step position to cause a first change in the breathing gas pressure during an unload portion of the current exhalation state based at least in part on the determined transition; and third means for changing the valve step position to cause a second change in the breathing gas pressure during a load portion of the current exhalation state based at least in part on the first predetermined breathing gas pressure value.

25. The apparatus of claim 24, the first determining means including:

means for determining a peak valve step position for a previous inhalation state of the previous breathing cycle;

means for starting a breath cycle timer after the peak valve step position for the previous breathing cycle is determined;

means for determining a peak valve step position for the current inhalation state; and means for stopping the breath cycle timer after the peak valve step position for the current inhalation state is determined.

26. The apparatus of claim 24, the second determining means including:

means for calculating a first transition variable based at least in part on an instantaneous valve step position;

means for calculating a second transition variable based at least in part on a peak valve step position; and means for identifying the transition from the current inhalation state to the current exhalation state after the first transition variable is less than or equal to the second transition variable.

27. The apparatus of claim 24, the second changing means including:

means for determining an unloading time associated with the unload portion of the current exhalation state and based at least in part on the determined breath cycle time;

means for beginning the unloading time after the transition from the current inhalation state to the current exhalation state;

means for decrementing the valve step position according to an unloading function until a second predetermined breathing gas pressure value is achieved; and means for changing the valve step position in response to a difference between the sensed breathing gas pressure and the second predetermined breathing gas pressure value after the second predetermined breathing gas pressure value is achieved and until the unloading time expires.

28. The apparatus of claim 24, the third changing means including:

means for determining a loading time associated with the load portion of the current exhalation state and based at least in part on the determined breath cycle time;

means for beginning the loading time after the unload portion of the current exhalation state;

means for incrementing the valve step position according to a loading function until the first predetermined breathing gas pressure value is achieved; and means for changing the valve step position in response to a difference between the sensed breathing gas pressure and the first predetermined breathing gas pressure value after the first predetermined breathing gas pressure value is achieved and until the loading time expires.

29. A method of providing a breathing gas, including:

a) sensing a parameter associated with delivery of the breathing gas;

b) adjusting a blower speed in response to a difference between the sensed parameter and a first predetermined value during an inhalation state of a breathing cycle;

c) detecting a transition from the inhalation state to an exhalation state of the breathing cycle based at least in part on the sensed parameter;

d) reducing the blower speed to drop a pressure associated with delivery of the breathing gas for a first time portion based at least in part on an exhalation unloading function; and e) increasing the blower speed to increase a pressure associated with delivery of the breathing gas for a second time portion based at least in part on an exhalation loading function until the sensed parameter exceeds the first predetermined value.

30. An apparatus for providing a breathing gas, including:

a variable speed blower adapted to pressurize the breathing gas;

a sensor adapted to sense a parameter associated with delivery of the breathing gas;

a controller in communication with the variable speed blower and the sensor and adapted to i) adjust the speed of the blower in response to a difference between the sensed parameter and a first predetermined value during an inhalation state of a breathing cycle, ii) detect a transition from the inhalation state to an exhalation state of the breathing cycle based at least in part on the sensed parameter, iii) reduce the blower speed for a first time portion of the exhalation state based at least in part on an exhalation unloading function, and iv) increase the blower speed for a second time portion of the exhalation state based at least in part on an exhalation loading function until the sensed parameter exceeds the first predetermined value.

31. An apparatus for providing a breathing gas, including:

a blower;

means for sensing a parameter associated with delivery of the breathing gas;

means for adjusting a blower speed in communication with the blower and sensing means wherein the adjusting is in response to a difference between the sensed parameter and a first predetermined value during an inhalation state of a breathing cycle;

means for detecting a transition from the inhalation state to an exhalation state of the breathing cycle in communication with the sensing means, wherein the detecting is based at least in part on the sensed parameter;

means for reducing the blower speed to drop a pressure associated with delivery of the breathing gas in communication with the blower and detecting means, wherein the reducing is for a first time portion of the exhalation state and based at least in part on an exhalation unloading function; and means for increasing the blower speed to increase a pressure associated with delivery of the breathing gas in communication with the blower and the reducing means, wherein the increasing is for a second time portion of the exhalation state and based at least in part on an exhalation loading function until the sensed parameter exceeds the first predetermined value.

* * * * *